US 12,279,784 B2

(12) United States Patent
Chu et al.

(10) Patent No.: US 12,279,784 B2
(45) Date of Patent: *Apr. 22, 2025

(54) MEDICAL HANDLE (71) Applicant: Boston Scientific Scimed, Inc., Maple Grove, MN (US)

(72) Inventors: Michael S. H. Chu, Brookline, MA (US); Kenneth W. Adams, Maynard, MA (US); Sharmad S. Joshi, Auburndale, MA (US); John Subasic, Stow, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/410,392

(22) Filed: Jan. 11, 2024

(65) Prior Publication Data

US 2024/0138867 A1    May 2, 2024

Related U.S. Application Data

(63) Continuation of application No. 17/449,007, filed on Sep. 27, 2021, now Pat. No. 11,903,600, which is a
(Continued)

(51) Int. Cl.
*A61B 17/221* (2006.01)
*A61B 1/307* (2006.01)
*A61B 17/00* (2006.01)

(52) U.S. Cl.
CPC ............ *A61B 17/221* (2013.01); *A61B 1/307* (2013.01); *A61B 17/00234* (2013.01);
(Continued)

(58) Field of Classification Search
CPC ..... A61B 1/00133; A61B 1/018; A61B 1/307; A61B 17/00234; A61B 17/221;
(Continued)

(56) References Cited

U.S. PATENT DOCUMENTS 4,372,295 A    2/1983   Heckele
6,551,327 B1 *  4/2003   Dhindsa ............... A61B 17/221
                                                    606/127
(Continued)

FOREIGN PATENT DOCUMENTS

CN        1602796 A      4/2005
CN      105358081 A      2/2016
(Continued)

OTHER PUBLICATIONS

Notice of Grant in Chinese Application No. 201980048829.X, dated May 2, 2024 (4 pages).
(Continued)

*Primary Examiner* — Jocelin C Tanner
(74) *Attorney, Agent, or Firm* — Bookoff McAndrews, PLLC (57) ABSTRACT

A retrieval device attachable to a scope includes a handle which has an attachment portion configured to couple the handle to the scope; a shaft coupled to the handle having a wire immovably coupled to the handle; and a sheath movable relative to the handle over the wire between a distal position and a proximal position via an actuator of the handle. The actuator actuates a slider assembly of the handle. The slider assembly is coupled to the sheath and movable relative to the attachment portion to move the sheath and an expandable end effector coupled to the distal end of the wire. The end effector is movable between a collapsed configuration when the sheath is moved distally to the distal position to cover the end effector and an expanded configuration when the sheath is moved proximally to the proximal position, uncovering the end effector.

20 Claims, 8 Drawing Sheets

Related U.S. Application Data continuation of application No. 16/502,773, filed on Jul. 3, 2019, now Pat. No. 11,154,315.

(60) Provisional application No. 62/712,649, filed on Jul. 31, 2018.

(52) U.S. Cl.
CPC ........... *A61B 2017/00358* (2013.01); *A61B 2017/00367* (2013.01); *A61B 2017/00477* (2013.01); *A61B 2017/00867* (2013.01); *A61B 2017/2215* (2013.01)

(58) Field of Classification Search
CPC .. A61B 2017/0034; A61B 2017/00358; A61B 2017/00367; A61B 2017/00477; A61B 2017/00867; A61B 2017/2215; A61B 2017/2913; A61B 2017/2915; A61B 2017/2916; A61B 17/22
See application file for complete search history.

(56) References Cited

U.S. PATENT DOCUMENTS

| | | | |
|---|---|---|---|
| 11,154,315 B2* | 10/2021 | Chu | A61B 17/00234 |
| 11,903,600 B2* | 2/2024 | Chu | A61B 17/00234 |
| 2003/0009176 A1 | 1/2003 | Bilitz | |
| 2004/0015050 A1 | 1/2004 | Goto et al. | |
| 2006/0116692 A1 | 6/2006 | Ward | |
| 2008/0009884 A1* | 1/2008 | Kennedy | A61B 17/221 606/127 |
| 2009/0105534 A1 | 4/2009 | Nakagawa et al. | |
| 2009/0157060 A1 | 6/2009 | Teague et al. | |
| 2009/0299344 A1 | 12/2009 | Lee et al. | |
| 2009/0312603 A1 | 12/2009 | Lam et al. | |
| 2012/0109186 A1 | 5/2012 | Parrott et al. | |
| 2014/0171735 A1 | 6/2014 | Galperin et al. | |
| 2014/0243594 A1 | 8/2014 | Raybin et al. | |
| 2014/0257253 A1 | 9/2014 | Jemison | |
| 2015/0119895 A1* | 4/2015 | Tah | A61B 17/221 606/127 |
| 2015/0164307 A1 | 6/2015 | Galperin et al. | |
| 2016/0143652 A1 | 5/2016 | Imai et al. | |
| 2016/0151080 A1 | 6/2016 | Sase et al. | |
| 2016/0166129 A1 | 6/2016 | Walish et al. | |
| 2016/0174956 A1 | 6/2016 | Ciulla et al. | |
| 2016/0213387 A1 | 7/2016 | Degraaf et al. | |
| 2017/0215901 A1 | 8/2017 | Harrah et al. | |
| 2018/0168672 A1 | 6/2018 | Chu | |
| 2018/0206863 A1 | 7/2018 | Chu | |
| 2018/0256180 A1 | 9/2018 | Tah et al. | |
| 2019/0208988 A1 | 7/2019 | Takatsuji et al. | |
| 2020/0023163 A1 | 1/2020 | Chu et al. | |

FOREIGN PATENT DOCUMENTS

| | | |
|---|---|---|
| CN | 106999202 A | 8/2017 |
| WO | 2018109979 A1 | 6/2018 |
| WO | 2018165507 A1 | 9/2018 |

OTHER PUBLICATIONS

Office Action in Chinese Application No. 201980048829.X, dated Dec. 9, 2023 (8 pages).

* cited by examiner

MEDICAL HANDLE

PRIORITY CLAIM

This application is a continuation of U.S. application Ser. No. 17/449,007, filed on Sep. 27, 2021, which is a continuation of U.S. application Ser. No. 16/502,773, filed on Jul. 3, 2019, now U.S. Pat. No. 11,154,315, which claims priority to U.S. Provisional Application No. 62/712,649, filed on Jul. 31, 2018. The disclosures of the above application(s)/patent(s) are incorporated herewith by reference.

FIELD

Aspects of the present disclosure generally relate to medical devices and procedures. Particular aspects relate to actuator devices and systems.

BACKGROUND

During noninvasive procedures, a physician may use a scope and a retrieval device to engage objects in a body. For example, in ureteroscopic procedures, the physician may use a ureteroscope and a retrieval device to engage stones, stone fragments, and/or other objects in a kidney, ureter, and/or bladder. One advantage of noninvasive procedures is that the body's normal openings and passages may be utilized. In ureteroscopic procedures, for example, the physician may move the scope through the ureter toward a stone, advance an end effector (e.g., a basket) of the retrieval device toward the stone, and engage the stone with the end effector to capture the object for removal from the body.

Many noninvasive procedures require at least two operators. For example, in ureteroscopic procedures, a first user (e.g., a physician) may control the scope while a second user (e.g., a physician's assistant) controls the retrieval device. A third operator may be required to manipulate the end effector. Requiring multiple operators increases the cost and complexity of these procedures and may lead to communication gaps between operators, movement inefficiencies during the procedure, and delayed response times. Aspects of this disclosure address these difficulties, and/or other aspects of the known treatment methods. For example, one aspect of the disclosure is to consolidate the ergonomic and operational control of the retrieval device and scope to a single hand. Another aspect is to allow a single one piece assembly of the medical device to the scope.

SUMMARY

The present embodiments are directed to a retrieval device configured to be attached to a scope device, the retrieval device system comprising a handle including an attachment portion configured to couple the handle to the scope device, a shaft including a drive wire and a sheath, the shaft being coupled to the handle, the sheath being movable over the drive wire between a distal position and a proximal position via an actuator assembly of the handle, the actuator actuating a slider assembly of the handle, the slider assembly coupled to the sheath and movable relative to the attachment portion of the handle to move the sheath, and an expandable end effector coupled to the distal end of the drive wire, the end effector movable between a collapsed configuration when the sheath is moved distally to the distal position to cover the end effector and an expanded configuration when the sheath is moved proximally to the proximal position, uncovering the end effector.

In an embodiment, the handle includes the actuator assembly, the actuator assembly comprising a lever and an arm configured to move the slider between a first position and a second position, the lever configured to rotate the arm about a pin such that a pin portion of the arm housed within a slot of the slider moves the slider along a longitudinal slider axis.

In an embodiment, the attachment portion is removably engageable with the scope device.

In an embodiment, the shaft extends from a proximal end coupled to the handle to a distal end configured to be positioned within a working channel of the scope device.

In an embodiment, the handle attachment portion is coupled to the scope device via a guide member, the handle movable relative to the guide member.

In an embodiment, the handle attachment portion includes a rod sized and shaped to be slidably received within a channel of the guide member such that the handle is movable relative to the guide member and the scope device along a longitudinal axis of the channel via the rod.

In an embodiment, the guide member includes one or more indents on an exterior surface thereof configured to receive a wedge portion of the handle to lock the handle in position relative to the guide member.

In an embodiment, the one or more indents is ramped to allow for proximal movement of the handle while preventing distal movement.

In an embodiment, the handle is rotatable about the guide member to allow for displacement of a longer length of the shaft within the working channel of the scope device.

The present embodiments are also directed to a retrieval device configured to be attached to a scope device, the retrieval handle device comprising an attachment portion configured to couple the handle to the scope device, a slider movable relative to the attachment portion of the handle to move a retrieval shaft coupled to the handle, and an actuator assembly comprising a lever and an arm configured to move the slider between a first position and a second position, the lever movable from a first position to a second position to rotate the arm about a pin such that a pin portion of the arm housed within a slot of the slider moves the slider along a longitudinal slider axis.

In an embodiment, the attachment portion is removably engageable with the scope device.

In an embodiment, the attachment portion is coupled to the scope device via a guide member, the handle movable relative to the guide member.

In an embodiment, the attachment portion includes a rod sized and shaped to be slidably received within a channel of the guide member such that the handle is movable relative to the guide member and the scope device along a longitudinal axis of the channel via the rod.

In an embodiment, the handle is rotatable about the guide to allow for displacement of a longer length of the shaft through the working channel of the scope device.

In an embodiment, the handle includes a spring member, the spring member biasing the lever to the first position and having a restoring force necessary to move the lever from the second position to the first position, and a second spring member, the second spring member biasing the sheath via a plunger to the first distal position and having a restoring force necessary to move the sheath from the second position to the first position.

The present embodiments are also directed to a method of retrieving tissue comprising inserting a distal portion of a retrieval device coupled to a scope device to a target area of a living body, the distal portion of the retrieval device sized and shaped to be inserted through the working channel of the scope device, the distal portion including: a shaft including a drive wire and a sheath, the shaft being coupled to a handle, the sheath being movable over the drive wire between a distal position and a proximal position via an actuator assembly of the handle, and an expandable end effector coupled to the distal end of the drive wire, the end effector movable between a collapsed configuration when the sheath is moved distally to the distal position to cover the end effector and an expanded configuration when the sheath is moved proximally to the proximal position, uncovering the end effector, actuating the actuator assembly of the handle to move the sheath proximally to uncover the end effector allowing the end effector to move from the collapsed configuration to the expanded configuration, capturing tissue, via the end effector, and retracting the end effector by releasing the actuator assembly such that the sheath moves distally to cover the end effector, wherein the retrieval device and the scope device are operated by a single user.

In an embodiment, the actuator assembly actuates a slider of the handle, the slider coupled to the shaft and movable relative to the handle to move the sheath.

In an embodiment, the actuator assembly comprises a lever and an arm configured to move the slider between a first position and a second position, the lever movable from a first position to a second position to rotate the arm about a pin such that a pin portion of the arm housed within a slot of the slider moves the slider along a longitudinal slider axis In an embodiment, the handle includes a spring member, the spring member biasing the lever to the first position and having a restoring force necessary to move the lever from the second position to the first position.

In an embodiment, the actuator assembly of the handle is operated with the index finger of one hand such that the scope device is held and a scope actuator is operated with a thumb of the same hand, simultaneously or independently.

BRIEF DESCRIPTION

DETAILED DESCRIPTION

The present disclosure may be further understood with reference to the appended drawings and the following description, wherein like elements are referred to with the same reference numerals. The present disclosure relates to retrieval devices and methods for retrieving material (e.g., tissue within a living body). Specifically, the present disclosure relates to a retrieval device that may be easily coupled with a ureteroscope device such as the LithoVue™. In an exemplary embodiment, the retrieval device includes a handle and an end effector. The end effector is utilized to engage stones, stone fragments, and/or other objects to be removed from kidneys, ureters, and/or bladder. It should be noted that the terms "proximal" and "distal", as used herein, are intended to refer to a direction toward (proximal) and away from (distal) a user of the device (e.g. physician).

Figure 1:
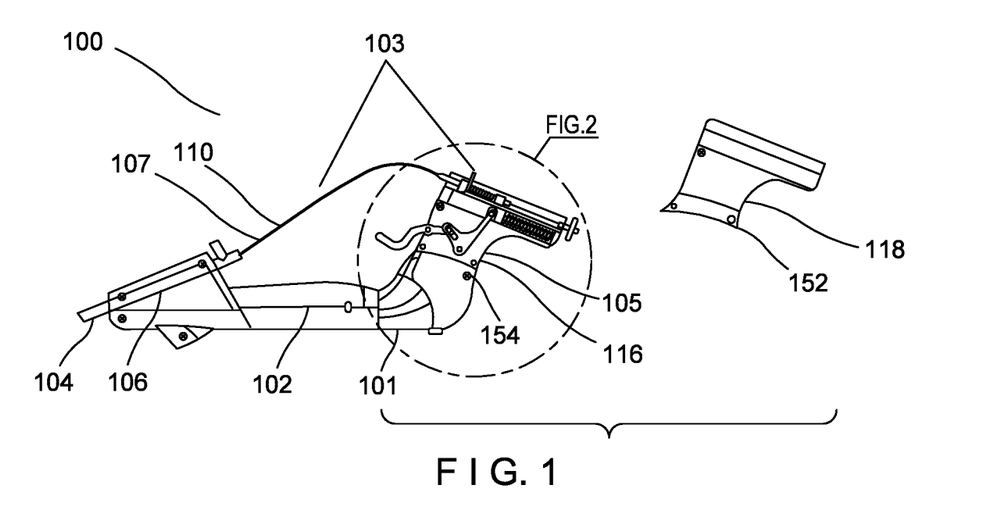
FIG. 1 shows a side view of a retrieval system according to a first exemplary embodiment of the present disclosure.
Figure 2:
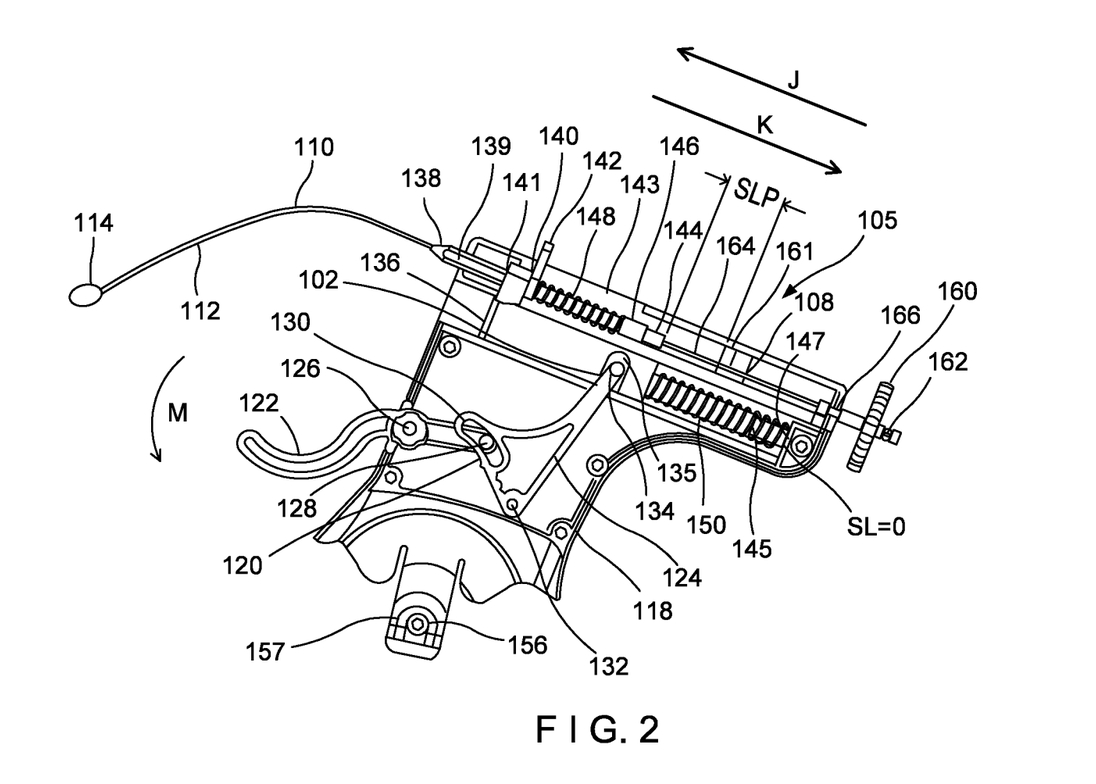
FIG. 2 shows a side view of a handle of the retrieval system of FIG. 1 according to an exemplary embodiment of the present disclosure.
Figure 3:
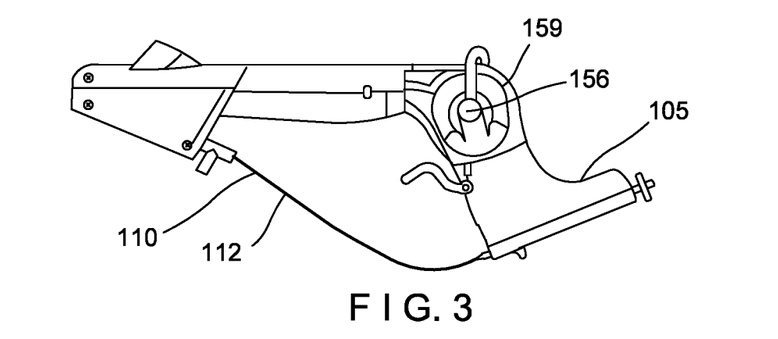
FIG. 3 shows a perspective view of the retrieval system of FIG. 1.
Figure 4:
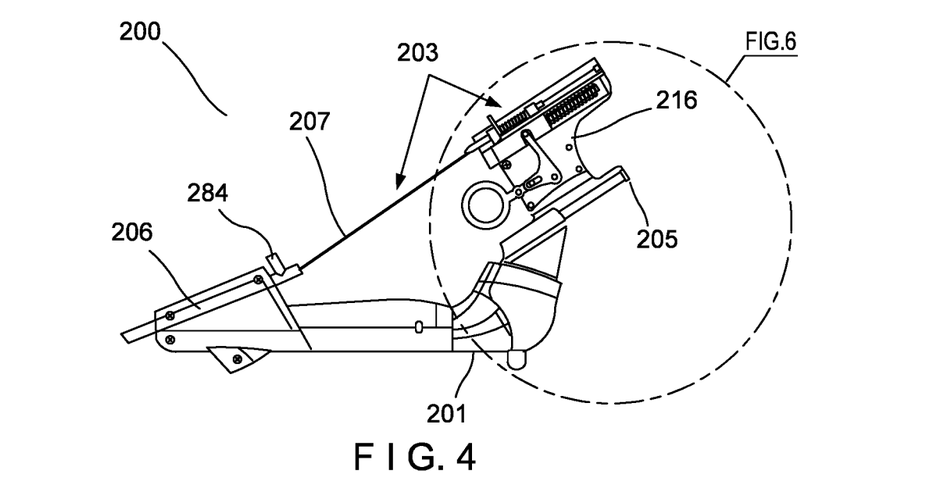
FIG. 4 shows a side view of a retrieval system according to a second exemplary embodiment of the present disclosure.
Figure 5:
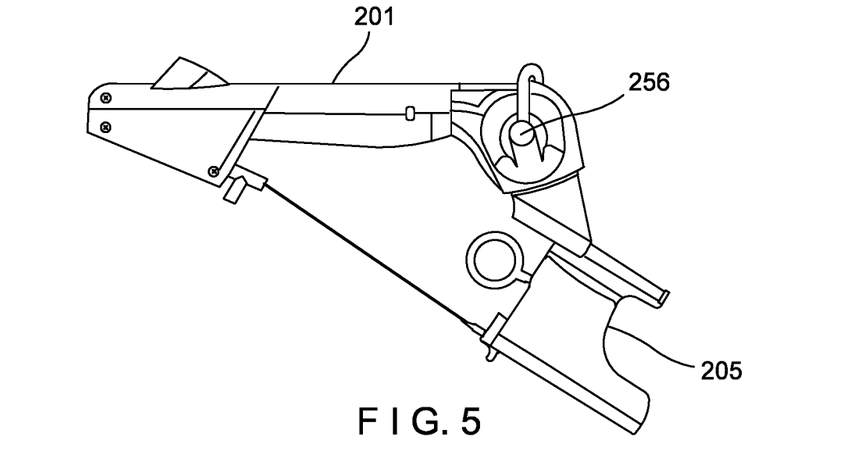
FIG. 5 shows another side view of the retrieval system of FIG. 4.

Referring to FIGS. 1-3, a retrieval system 100 includes a scope 101 and a retrieval device 103. The retrieval device 103 includes a handle assembly 105 and an end effector assembly 107. The handle assembly 105 is configured to be attached to the scope 101, as depicted in the figures. The scope 101 may comprise any scope configured for use in minimally invasive procedures, a ureteroscope, for example, under the brand name LithoVue™. As shown in FIG. 1, a scope 101 includes a scope body 102 extending a long a scope axis between a proximal end that remains outside the body during use and a distal end inserted into the body (e.g., through a natural body lumen accessed via a natural body opening). A scope sheath 104 extends distally from the distal end of this exemplary scope body 102. A working channel 106 extends through the scope body 102 and the scope sheath 104, allowing a drive wire 108 of the end effector assembly 107 (e.g., a wire, thread, rod or similar elongated element) to be advanced through the scope 101 to a treatment site in a body, such as the interior of a kidney. In some aspects, the scope 101 comprises an actuator configured to manipulate the scope sheath 104.

The end effector assembly 107 includes a shaft 110, composed of the drive wire 108 and a sheath 112, and an end effector 114 attached to a distal end of the drive wire 108. The sheath 112 is sized and shaped to cover and slide over a portion of the drive wire 108 and the end effector 114. The sheath 112 is substantially the same length as the drive wire 108 plus enough extra length to cover the end effector 114. In an exemplary embodiment, the length of the shaft 110, including the drive wire 108 and sheath 112, does not extend significantly past the distal end of the scope working channel 106. This allows the shaft 110 to become substantially a straight line between the handle assembly 105 and working channel 106 of the scope 101, creating a true non-retracting end effector. However, in other embodiments, the shaft 110 may be substantially longer than the scope working channel 106. In this embodiment, the shaft 110 may be coiled in a loop, as shown in FIG. 1. In another example, the shaft 110 may be only slightly longer than the working channel 106 of the scope. In this embodiment, the slack of the shaft 110 may be displaced as a bump, as shown in FIG. 3. If there is extra length, the length of the shaft 110 extending from a distal end of the working channel 106 can be adjusted at the proximal end of the handle assembly 105 by the user's hand that is not gripping the handle assembly 105. The end effector 114, in this embodiment, is a self-expandable basket made of a shape memory material, similar to those sold by Boston Scientific® under the brand name Zero Tip®. In another embodiment, the end effector 114 may be formed of wires forced or constrained to form a basket shape, similar to the Boston Scientific Dakota®.

The handle assembly 105, as best seen in FIG. 2, includes a handle body 116 comprising two covers 118. The handle body 116 is coupled to the shaft 110 via the drive wire 108 and includes an actuator assembly 120 comprising a lever 122 and an arm 124. The actuator assembly 120 is configured to move the sheath 112, via a plunger, a first spring, and a sliding assembly, relative to the end effector 114 to cover and collapse the end effector 114 or to expose and expand the end effector 114. Specifically, to retract the sheath 112, the lever 122 is depressed in the direction of arrow M, clockwise about a first pin 126, causing a second pin 128 to rotate counter-clockwise in a slot 130 of the arm 124. This movement of the second pin 128 within the slot 130 causes the arm 124 to rotate clockwise about a third pin 132 which in turn rotates a pin portion 134 of the arm 124 proximally.

As can be seen in FIG. 2, the pin portion 134 of arm 124 is positioned within a slot 135 of a slider 136 which is movable proximally and distally relative to the handle body 116. Thus, rotational movement of the pin portion 134 of the arm 124 causes the slider 136 to move proximally and distally, which in turn retracts the sheath 112 that is coupled to a spring biased plunger 138, moving the sheath 112 proximally to expand the end effector 114 or distally to collapse the end effector 114. Specifically, proximal movement of the pin portion 134 moves the slider 136 proximally, pulling the plunger 138, via wall 140 extending from the slider 136, and the attached sheath 112 to uncover the end effector 114, allowing it to expand. As depicted in FIG. 2, the plunger 138 may be substantially cylindrical with two flat sides 139 and is sized and shaped to slide in a channel 141 having a matching profile and extending through the wall 140. The plunger 138 also includes a trigger 142 sized and shaped to be moved through an upper opening 143 in the handle body 116 via a thumb or finger of the user. A support tube 144 extends proximally from a proximal end of the plunger 138 and is sized and shaped to be slid through a block 146. A first compression spring 148 is positioned about the outer diameter of the support tube 144 in a compressed state between the proximal end of the plunger 138 and the distal end of the block 146. The first spring 148 is at its initial height and exerts an initial restoring force to bias the sheath 112 to a normally distal position, such that the distal side of the trigger 142 abuts the wall 140.

The first spring 148 is most often used to prevent damage to the fragile end effector 114 and sheaths 112 such as the Zero Tip™ and the Dakota™, which are both less than 3 French in shaft diameter. In use, the compressed first spring 148 biases the plunger and sheath 112 distally. The trigger 142 can be used to manually pull the sheath 112 more proximally than the slider can to further withdraw the sheath 112 and uncover the end effector 114 to a larger open state. This action allows stuck or oversized burdens to be released quickly from the end effector 113. The first spring 148 also returns the plunger 138 and the sheath 112 distally when the hand force is removed from the trigger 142. In this case, the first spring 148 will further compress to a second load height as the slider 136 and sheath 112 are moved distally to firmly close and capture the burden within the end effector 114. More specifically, the sheath 112 and plunger 138 are moved distally in conjunction with the slider 136 until the sheath 112 and plunger 138 advancement is stopped by the abutment of the end effector 114 with the captured burden. With the sheath 112 and plunger 138 stopped, further advancement of the slider 136 distally will create a force greater than the initial force of the first spring 148 to compress the first spring 148 a distance x to a second load height. In turn, the distally extending length of the sheath 112 is shortened as the first spring 148 is compressed to its second load height. The second load is greater in magnitude than the initial load of the first spring 148. The first spring 148 is calculated to a preferred second load (F) relative to the maximum capturable size, (converted to a linear displacement x) (where K in Hooke's Law F=−Kx is known) such that the second spring load is insufficient to cause damage to the end effector or the sheath. Fi is also known as the grip force of the end effector 114. In other embodiments, the second load is calculated to provide sufficient force to strangulate or to provide cutting.

Full depression of the lever 122 simultaneously causes a proximal end of a stroke limiter 145 coupled to a proximal end of the slider 136 to reach a proximal wall 147 of the handle assembly 105. When the stroke limiter 145 abuts the proximal wall 147, the sheath 112 is incapable of being retracted any further via the lever 122 and the end effector 114 is, at this point, functionally opened. Thus, the handle 105 has an end effector stroke length SL determined by the distance between the proximal end of the stroke limiter 145 and the distal face of the proximal wall 147. However, in some embodiments, the end effector 114, such as the Dakota™ or the Escape™ end effectors, can be opened further via the trigger 142. The trigger 142 is pulled proximally through the handle body 116 (composed of covers 118) to further retract the sheath 112 and further expand the end effector 114. The further retraction or expansion of the end effector 114 is used to release trapped or stuck stones within the end effector or to quickly reposition stones, respectively. When the trigger 142 is released, the first spring 148 returns the plunger 138 to its initial position. The specific distance that the trigger 142, and thus the sheath 112, may be moved proximally is controlled by the support tube 144, which may be cut to a predetermined length to control the stroke length of the plunger 138.

The lever 122, sheath 112, plunger 138, slider 136, and arm 124 are returned back to their initial positions (i.e., where the end effector 114 is covered by the sheath 112) when the hand force on lever 122 is removed and no burden (i.e., kidney stone, tissue, foreign object, etc.) is captured. A second spring 150 positioned around the stroke limiter 145 between the proximal wall 147 and the proximal end of the slider 136 provides the restoring force necessary to return each element to its starting position when the hand force is removed from the lever 122. The second spring 150 is selected to be stiffer than the first spring 148. Therefore, the second spring 150 is configured to provide a force more than sufficient to close the end effector 114 while the first spring 148 controls the specific magnitude of force (i.e., to close the end effector, capture debris, or to cut a burden). When the hand force is removed from the lever 122, the restoring force of the second spring 150, which is compressed from its initial length by the slider 136, forces the slider 136 back to its initial distal position, thereby forcing the spring 148, biased plunger 138, sheath 112, and arm 124 to their initial positions (i.e., positions without a burden). That is, the restoring force of the second spring 150 provides the force exerted on the end effector 114 via the proximal end of the plunger 138 and/or the sheath 112 via the first spring 148 for closure, capture or strangulation of a burden (i.e., a second, burdened position). The stiffness of the first spring 148 is be pre-selected to, for example, increase the durability of the end effector 114, control the specific magnitude of the end effector grip to a stone burden, or to control the strangulation force during tissue cuts. As will be understood by those skilled in the art, a spring will exert a known force at a given spring deformation (Hook's Law). In contrast, hand force applied to the end effector 114 relies, for example, on tactile feel of the user to gauge the magnitude of force applied and may vary from person to person. If further closure/covering of the end effector 114 is desired, the trigger 142 of the plunger 138 may be moved distally, moving the sheath 112 further distally over the end effector 114 to, for example, capture a small stone or debris in a tortuous pathway.

In an exemplary embodiment, the handle assembly 105 is configured without a first spring 148. In this embodiment, the second spring 150 applies its restoring force directly to the end effector 114, simplifying the mechanics of the handle assembly 105. In one example of this embodiment, the plunger 138 and the support tube 144 are glued or otherwise coupled to the slider 136. In another example, the slider 136 is molded with the plunger 138 and the support tube 144 to create a single part. In this example, both the first spring 148 and the trigger 142 are removed. It will be understood that these embodiments allow for a simpler handle assembly 105 with less component parts involved in the extension and retraction of the sheath 112 and will not have the benefits of the first spring 148.

The handle assembly 105 may be removably attached to the scope 101 at an attachment portion 153 by positioning a first pin 152 of the covers 118 into a screw hole 154 of the scope body 102 and snapping a second pin 156 of the covers 118 into a center hole 157 of a deflection knob 159 of the scope body 102. To release the handle assembly 105 from the scope body 102, the second cover pin 156 is first removed from the center hole 157 and the first cover pin 152 is subsequently removed from the screw hole 154.

The drive wire 108 extends through the plunger 138 from a distal end of the handle assembly 105, through a handle lumen 161, to a knob 160 located at a proximal end of the handle 20. The drive wire 108 is attached to the knob 160 in this embodiment by a set screw 162. A handle cannula 164, such as a stainless steel hypotube, is used to sleeve the proximal end of the drive wire 108 inside the handle assembly 105 to increase stiffness of the drive wire 108, preventing kinking as components of the handle assembly 105 are manipulated over the drive wire 108. The knob 160 can be rotated about a hole 166 formed by mating handle covers 118 together. Rotation of the knob 160 within the hole 166 rotates the drive wire 108 and thus, the end effector 114 attached to the distal end thereof.

In an exemplary embodiment, the handle assembly 105 may include an electrosurgical feature. For example, an active plug may be connected to the proximal end of the drive wire 114 proximally of the knob 160. In another example, the active plug may be positioned at the proximal end of the handle assembly 105 in lieu of the knob 160 if rotation of the end effector 114 is not required.

A retrieval system 200, according to another exemplary embodiment of the present disclosure is depicted in FIGS. 4-8. The retrieval system 200 is substantially similar to retrieval system 100, including a scope 201 and a retrieval device 203 comprising a handle assembly 205 and an end effector assembly 207, except as described herein. Specifically, the handle assembly 205 is movable relative to the scope 201 via a guide 268, as will be described in further detail below.

Figure 6:
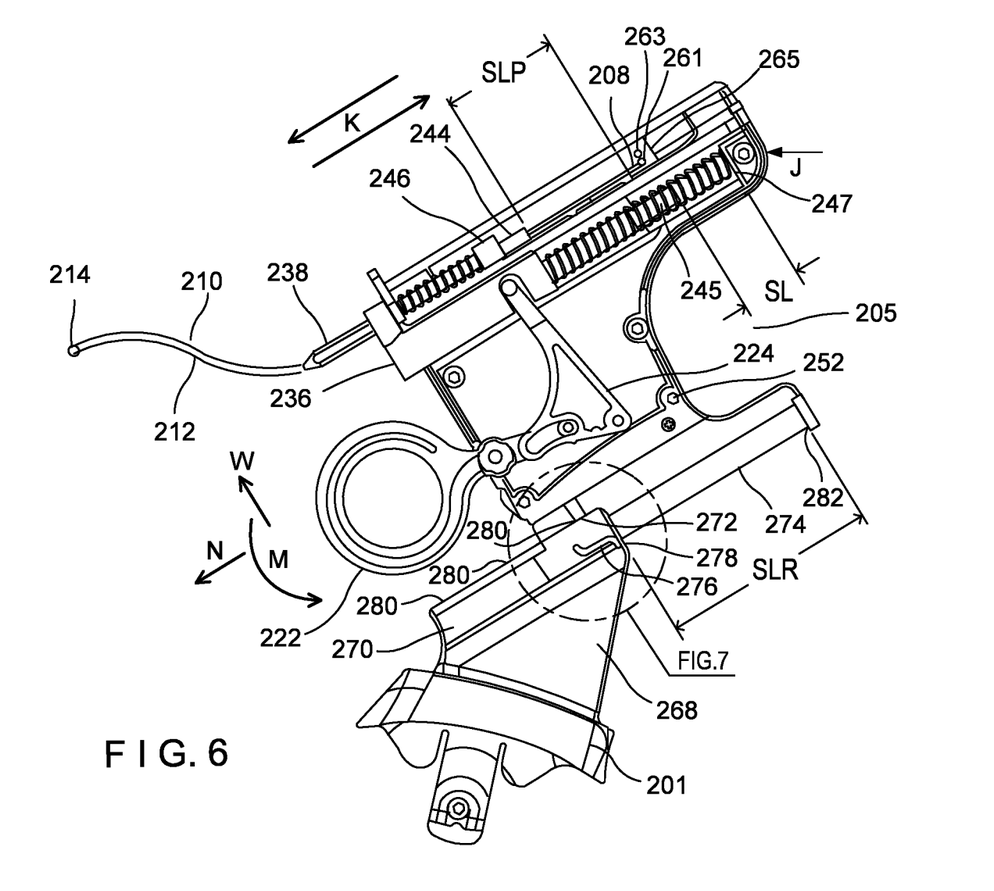
FIG. 6 shows a side view of a handle and guide of the retrieval system of FIG. 4 according to an exemplary embodiment of the present disclosure.

The handle assembly 205, in this embodiment, includes a 360-degree closed lever ring 222 in lieu of a lever 122 as found in the handle assembly 105. FIG. 6 depicts the lever ring 222 in a non-depressed state such that the slider 236, plunger 238, arm 224 and shaft 210 are in their distal position with the end effector 214 in the closed or collapsed position. The handle assembly 205 has an end effector stroke length SL determined by the distance between the proximal end of the stroke limiter 245 and the distal face of the proximal wall 247. The plunger 238, similarly to the plunger 138, has a stroke length SLP determined by the distance between the proximal end of the support tube 244 and the distal end of the anchor block 246. Thus, stroke lengths SL and SLP can be custom sized by cutting the stroke limiter 245 and the support tube 244, respectively, to a predetermined length.

In this embodiment, a slide mechanism allows the handle assembly 205 to slide proximally and distally relative to the scope 205. Specifically, the handle assembly 205 of this embodiment includes a guide 268 mounted onto the scope 30 using cover pins 252 and 256 as described above with respect to cover pins 152, 156. The guide 268 includes a channel 270 positioned at a preferred angle relative to the scope 201. The channel 270 is open to a slot 272 that extends along its length. In a preferred embodiment, the channel 270 has a circular profile configured, for example, to match the outer profile of a circular rod 274 positioned on the handle body 216. Thus, the handle 205 is movable relative to the guide 268 and the scope 201 along a longitudinal axis of the channel 270 via the circular rod 274, which is slidable within the channel 270. The rod 274, in an embodiment, includes a cantilever latch 276 configured to lock to a proximal wall 278 of the guide 268. The cantilever latch 276 prevents the rod 274 from sliding proximally out of the channel 270 once the rod 274 and latch 276 have been inserted therein distally past the wall 278. In an exemplary embodiment, the rod 274 has a diameter slightly smaller than an inner diameter of the channel 270 such that there is a smooth interface between the two components. However, in another embodiment, the channel 270 may have a diameter slightly smaller than an outer diameter of the rod 274, creating an interference fit between the rod 274 and the channel 270. One skilled in the art will understand that while the rod 274 and the channel 270 of the present embodiment have circular profiles, any shape profile may be used such as, for example, square, oval, polygonal, etc. Furthermore, the interface between the rod 274 and the channel 270 may include a locking mechanism, as described in further detail below.

Figure 7:
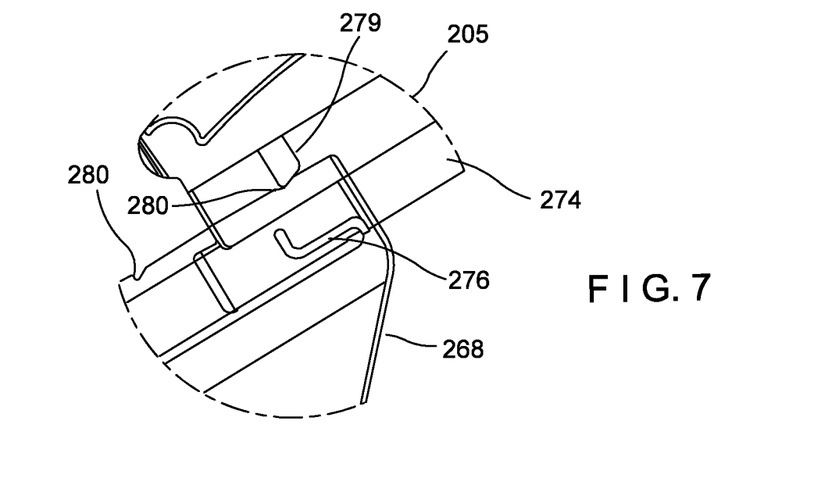
FIG. 7 shows an exploded view of a portion of the handle of FIG. 6.
Figure 8:
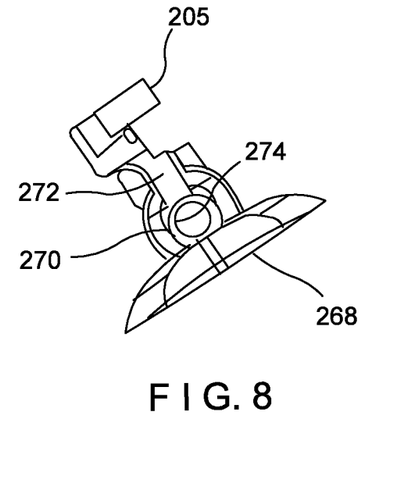
FIG. 8 shows an exploded front view of the sliding rod and channel of the handle and guide, respectively, of the retrieval system of FIG. 4.

Still looking at FIG. 6, the rod 274 of this embodiment is made with a relatively smaller diameter than the channel 270 of the guide 268, allowing the handle assembly 205 to cock or tilt relative to the guide 268 in the direction of arrow M. Specifically, the handle assembly 205 includes a wedge portion 279 that interacts with the guide 268 so that, due to the angle of the channel 270 and the center of mass of the handle assembly 205, a user may tilt the handle assembly 205 using the lever ring 222. The guide 268 includes three indents 280 on an exterior surface thereof that are configured to receive the wedge portion 279 of the handle 205, locking the handle assembly 205 in position relative to the guide 268 and the scope 201. The lever ring 222, with its 360-degree closed ring, allows the user to lift the ring 222 with, for example, the nail side of the index finger, to lift the handle assembly 205 in the direction of arrow W, as shown in FIG. 6. This lifting of the lever ring 222 and thus, the handle assembly 205, moves the wedge portion 279 out of the indents 280, allowing the handle assembly 205 to slide proximally or distally relative to the guide 268. As can be seen in FIG. 7, the indents 280 of this embodiment may be ramp-shaped with a depth of each indent 280 increasing the distal direction. Thus, the handle assembly 205 is able to be moved proximally without being lifted away from the indents 280. However, in other embodiments, the indents 280 may be substantially U-shaped such that the handle assembly 205 must be lifted to free the wedge portion 279 from the indents 280 and move the handle assembly 205. As can be seen in FIG. 6, the rod 274 may include a proximal stop 282 with a larger diameter than the rod 274 and the channel 270. The stop 282 prevents the rod 274 from sliding proximally out of the channel 270 by abutting against a proximal surface of the channel 270.

Movement of the handle assembly 205 relative to the guide 268 (i.e., via sliding) moves the sheath 212, drive wire 208 and end effector 214 a corresponding and equal distance and direction. For example, at a proximal-most position, a stroke length of the rod, SLR, is defined with the distal tip of the sheath 212 and end effector 214 positioned flush with the distal end of the scope working channel 206. When the handle assembly 205 is moved distally such that SLR is equal to zero, the tips of the sheath 212 and end effector 214 are extended a distance of SLR from the end of the insertion device working channel 206.

Referring to FIG. 3, it can be seen that the handle assembly 205 is angled toward a T-connector 284 of the scope 10. In a preferred embodiment, this angulation allows for there to be no slack in the shaft between the plunger 238 and the T-connector 284. Thus, retraction of the sheath 212 to open the end effector 214 or extension of the sheath 212 to close/collapse the end effector 214 will result in a truly non-retracting end effector 214 because the entire reciprocal movement between the drive wire 214 and the sheath 212 is transmitted only by the sheath 212 while the end effector 214 remains stationary.

In an exemplary embodiment, the handle assembly 205 of the retrieval device 203 does not include an end effector rotation feature (i.e., knob). Rather, in this embodiment, the proximal end of the drive wire 208 is secured to the block 246 as the drive wire 208 is bent from the handle lumen 261 and into second lumen 263 to secure the drive wire 208 in place. During assembly, the drive wire 208 can be trimmed to a predetermined length to allow a tab 265 of the handle body 216 to push and bend the proximal end of the drive wire 208, securing it in place.

Figure 9:
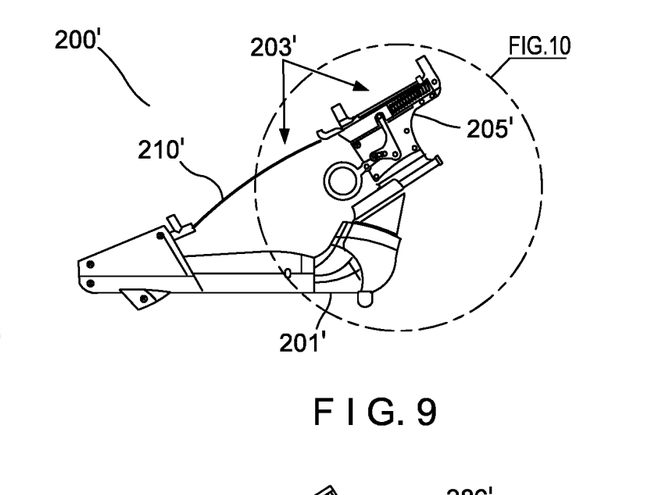
FIG. 9 shows a side view of a retrieval system according to a third exemplary embodiment of the present disclosure.
Figure 10:
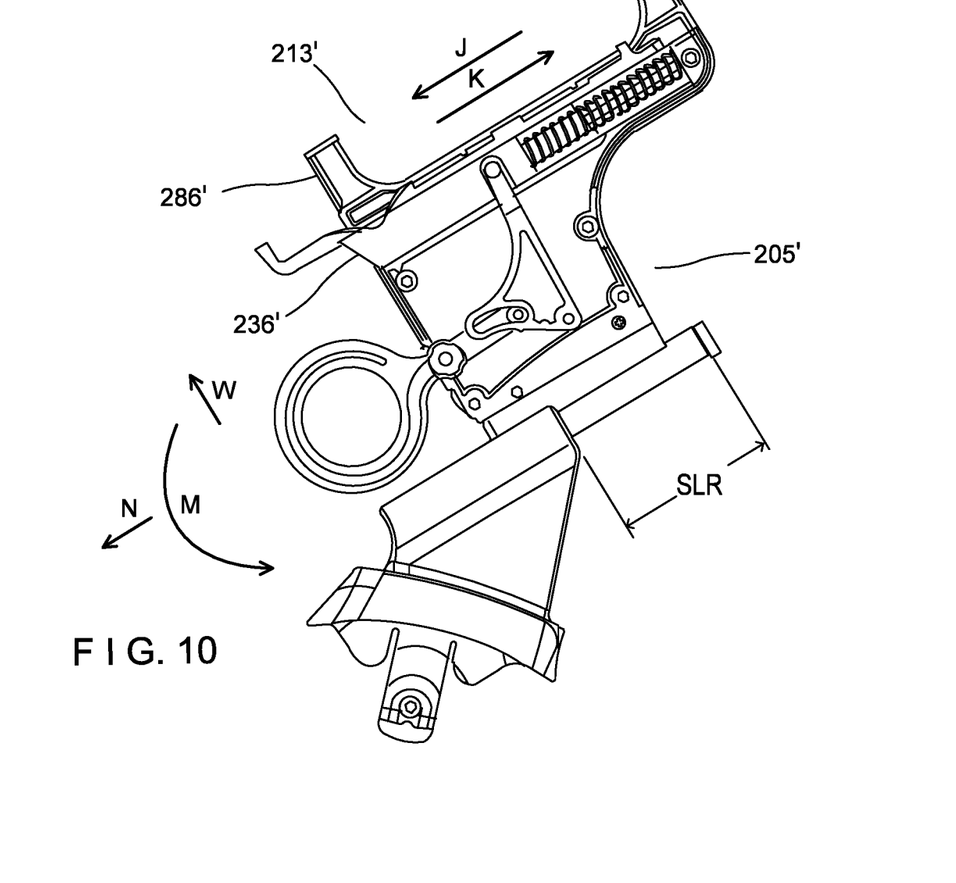
FIG. 10 shows a side view of a handle and guide of the retrieval system of FIG. 9.
Figure 11:
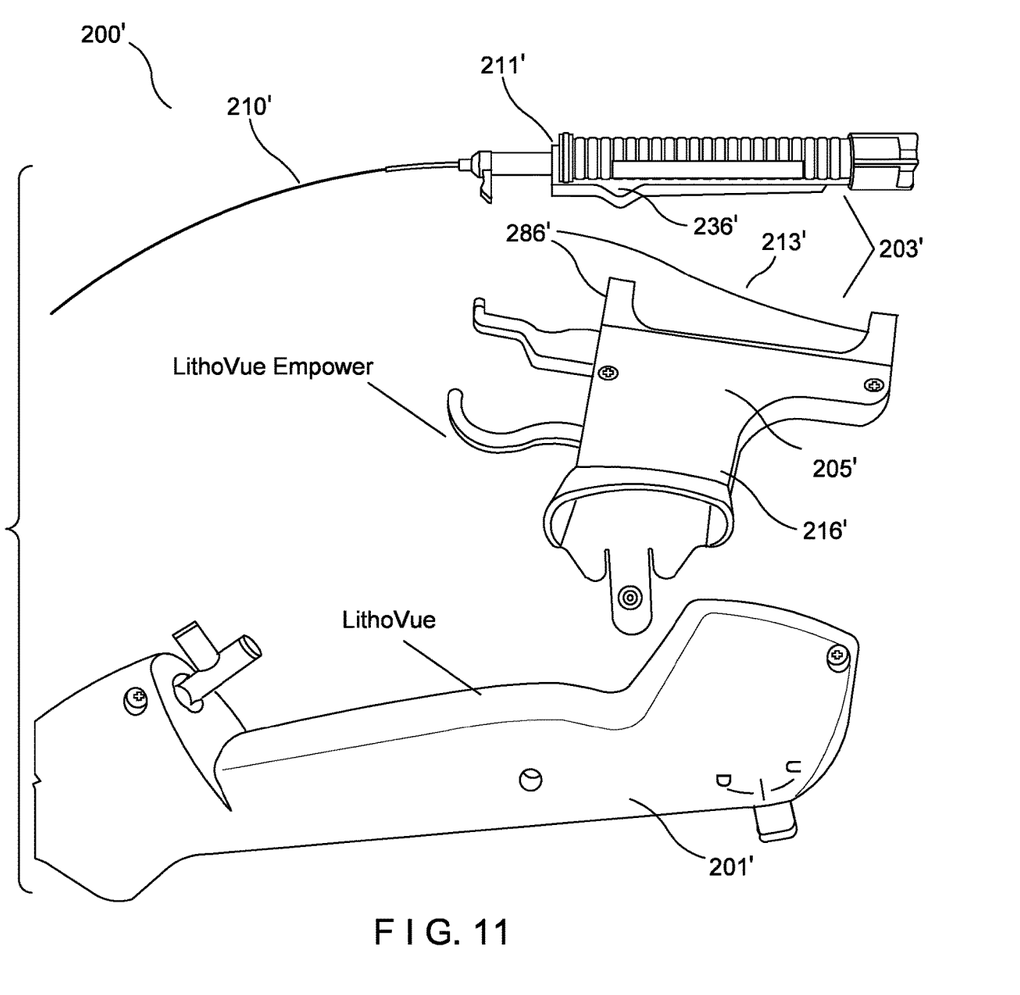
FIG. 11 shows a top view of the retrieval system of FIG. 9.

A retrieval assembly 200', according to another exemplary embodiment of the current disclosure, is depicted in FIGS. 9-11. The retrieval assembly 200' is substantially similar to retrieval assembly 200, except as described herein. Specifically, the shaft 210' of the retrieval device 203' of the retrieval assembly 200' is separable from the handle assembly 205' and the handle body 216' and includes a shaft handle 211' extending proximally therefrom. That is, the shaft handle 211' is configured so that it may be clipped into a shaft handle attachment portion 213' of the handle assembly 205'. As can be seen in FIG. 10, the handle assembly 205' includes two clips 286' forming the shaft handle attachment portion 213' of the handle assembly 205'. The shaft handle 211', which may, for example, be a Segura® handle or similar device, may be snapped into the clips 286' to couple the slider 236' to the handle assembly 205'. Once the shaft handle 211' has been positioned within the attachment portion, the user is able to position (i.e., extend/retract) the shaft 210' within the working channel 206' of the scope 201' by gripping the shaft handle 211' and sliding it proximally or distally within the attachment portion. The end effector 214' may be expanded and/or retracted as described above with respect to retrieval assembly 200'.

Figure 12:
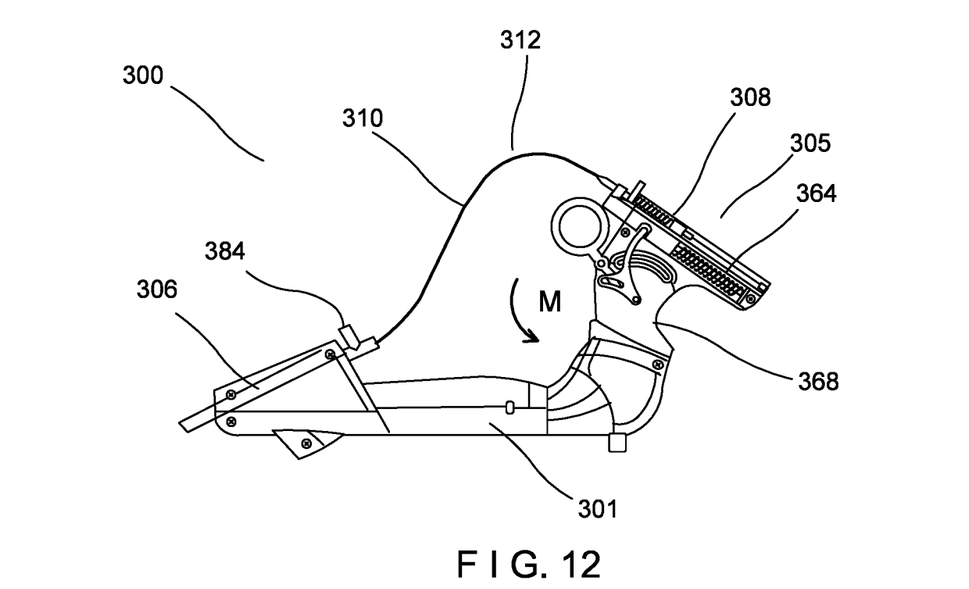
FIG. 12 shows a side view of a retrieval system according to a fourth exemplary embodiment of the present disclosure.
Figure 13:
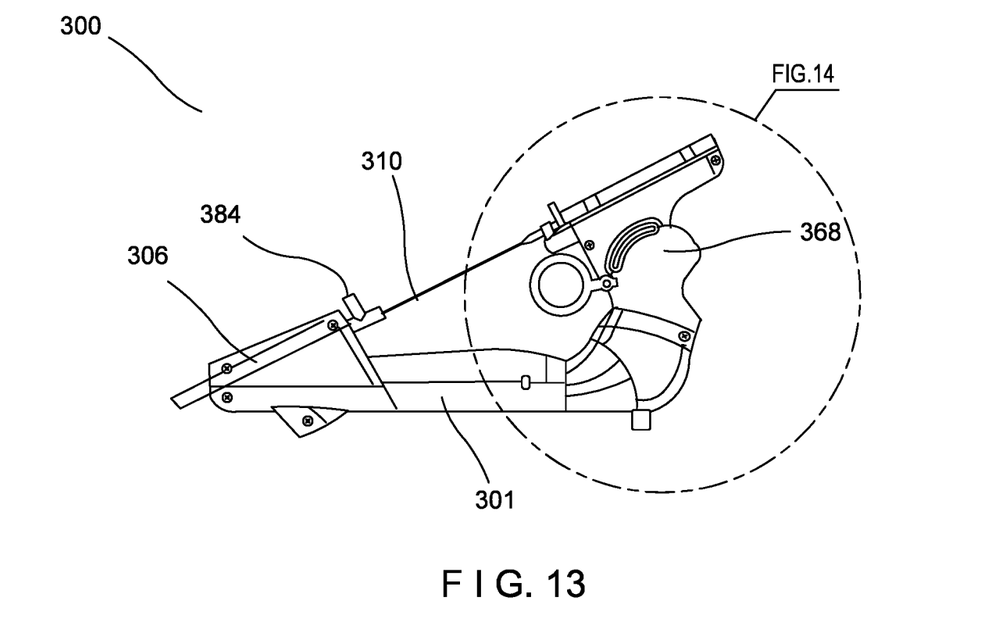
FIG. 13 shows another side view of the retrieval system of FIG. 11.
Figure 14:
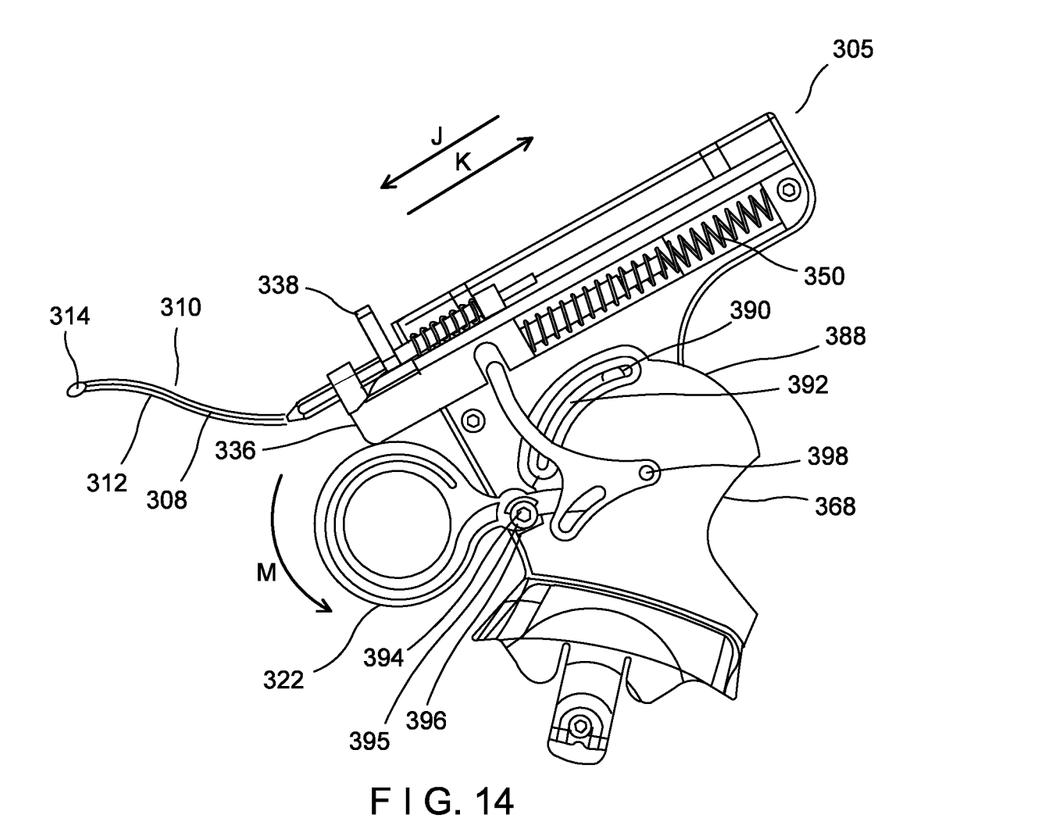
FIG. 14 shows a side view of a handle and guide of the retrieval system of FIG. 11 according to an exemplary embodiment of the present disclosure.
Figure 15:
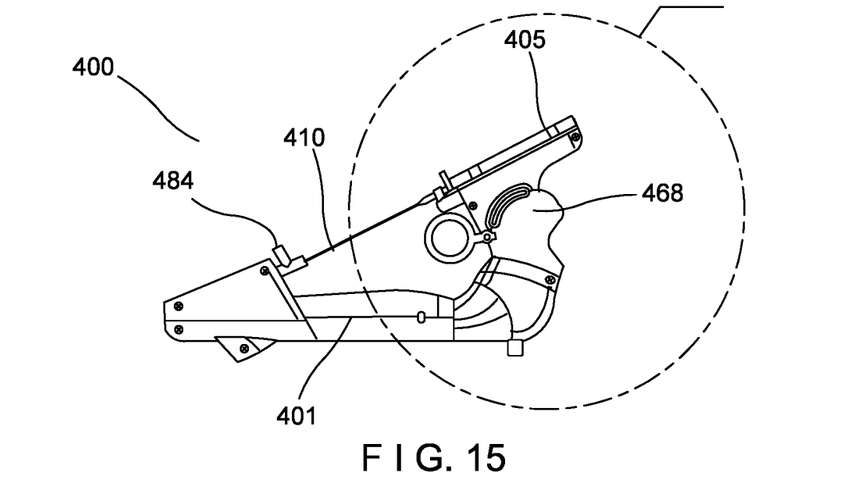
FIG. 15 shows a side view of a retrieval system according to a fifth exemplary embodiment of the present disclosure.
Figure 16:
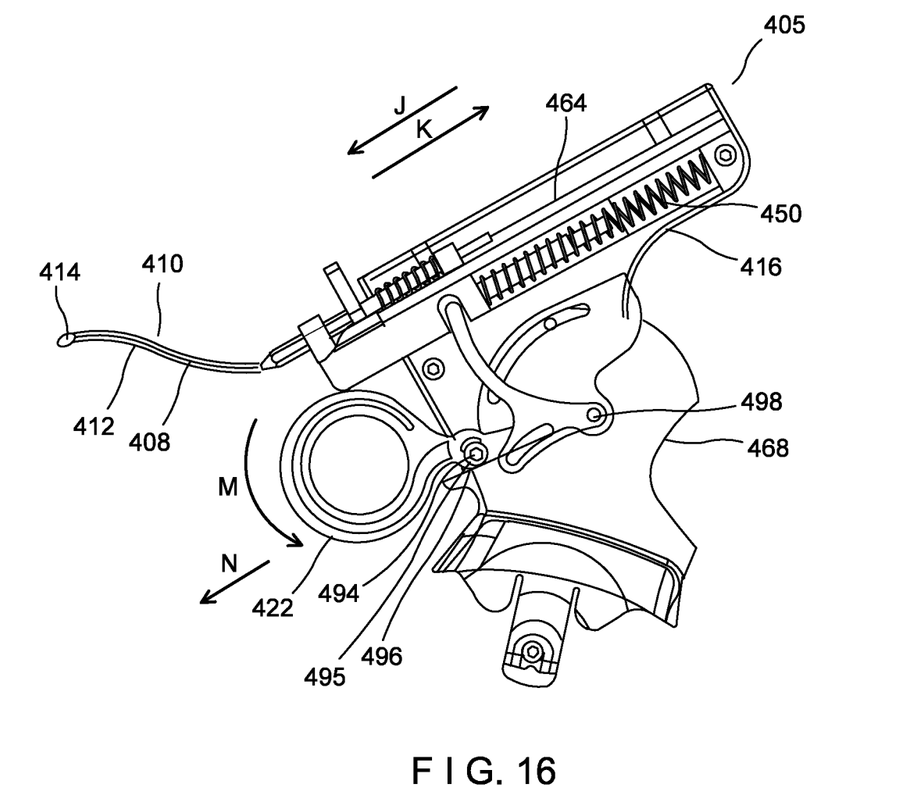
FIG. 16 shows a side view of a handle and guide of the retrieval system of FIG. 14 according to an exemplary embodiment of the present disclosure.

A retrieval assembly 300, according to another exemplary embodiment of the current disclosure, is depicted in FIGS. 12-14. The retrieval assembly 300 is substantially similar to retrieval assembly 200, except as described herein. Specifically, the handle assembly 305 of this embodiment is configured to rotate about the guide 368 allowing for displacement of a longer length of the shaft 310 within the working channel 306 of the scope 301 and out the distal end of the scope 301. FIGS. 12-13 illustrates the handle assembly 305 coupled to the scope 301 via the guide 368. The shaft 310 of this embodiment comprises the outer sheath 312 and drive wire 308 stiffened with a hypotube 364 at the proximal end. The hypotube 364 extends from inside the handle assembly 305 to an inside of the T-connector 384. This increase in stiffness in the proximal shaft 310 aids in advancing the shaft 310 into the T-connector 384 so that the shaft 310 straightens or becomes linear as the handle assembly 305 is rotated toward the T-connector 384. FIG. 12 depicts the handle assembly 305 in the retracted shaft position with the distal tip of the shaft 310 situated just proximal to the distal deflection zone of the scope working channel 306. However, in this embodiment, moving the lever ring 322 in the direction of arrow M, as depicted in FIG. 13, rotates the handle assembly 305 and the attached shaft 310 towards the T-connector 384 such that the distal tip of the shaft 310 is advanced in the working channel 306 of the scope 301 and eventually out of the distal end of the working channel 306.

Specifically, the guide 368 of this embodiment includes a circular surface 388 with a pin 390 that interfaces with an arced slot 392 of the handle assembly 305 and a pin 398 which provides an axis of rotation. When the handle assembly 305 is coupled to the guide 368, the pin 390 is positioned within the slot 392 so as to be slidable along a length thereof to rotate the handle assembly 305 such that an angle between the handle assembly 305 and the scope 301 is increased or decreased. The degree to which the angle between the handle assembly 305 and the scope 301 can be increased or decreased is limited by the length of the slot 392. When the pin 390 abuts a proximal end of the slot 392, in this embodiment, the handle assembly 305 is angled so that a straight line is formed between the plunger 338 and the T-connector 384. Thus, the shaft 310 is straightened (i.e., without any slack) and the retrieval device 303 includes a true non-retracting end effector/basket. Angulation of the handle assembly 305 relative to the guide 368 is controlled by the ring lever 322. The ring lever 322 of this embodiment includes a pin 394 with a surface 395 just proximal thereof configured to abut a stop or ledge 396. FIG. 14 depicts the pin 394 abutting the stop 396. At this point, the angle between the handle assembly 305 and the scope 301 is at its smallest with the pin 394 abutting the proximal end of the slot 392. Further movement of the lever 322 about pin 394, in the direction of arrow M, when the pin 394 and the stop 396 are abutting, moves the slider 336 and the attached sheath 312 in the proximal direction to open the end effector 314. When the hand force is removed, the lever ring 322 and the second spring 350 return the end effector 314 to the closed position to capture the burden. The shaft 310 is retracted from the distal end of the scope 301 by moving the lever ring 322 in a opposite direction of arrow M. Maximum retraction of the device shaft 310 and the handle assembly 305 occurs when the pin 390 abuts a distal end of the slot 392.

A retrieval assembly 400, according to another exemplary embodiment of the current disclosure, is depicted in FIGS. 14-17. The retrieval device 400 is substantially similar to retrieval assembly 300, except as described herein. In this embodiment, the shaft 410 is both rotatably and linearly movable via the handle assembly 405. Specifically, the two movements are used in sequence with the first rotational movement being for gross/large unrefined extension of the shaft 410 and the second linear movement being for fine adjustment of the shaft 410. The fine adjustment can be used to position the end effector 414 closer to, for example, a kidney stone without moving the scope sheath 404.

Figure 17:
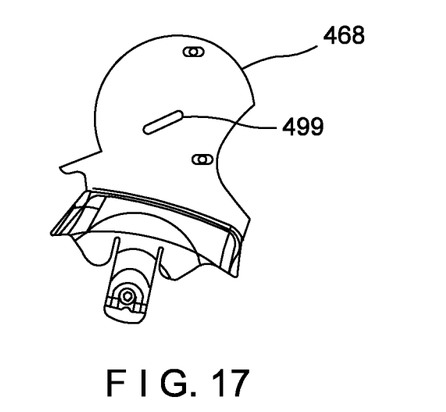
FIG. 17 shows a side view of the guide of the retrieval system of FIG. 14 according to an exemplary embodiment of the present disclosure.

Similar to the embodiment of retrieval device 300, the proximal end of the drive wire 408 is supported with a hypotube 464, as described above. The distal tip of the shaft 410 can be advanced through the working channel 406 of the scope 401 and eventually out the distal end of the scope sheath 404 by moving the lever ring 422 in the direction of arrow M to rotate the handle assembly 405 and the attached shaft 410 toward and into the T-connector 484. However, in this embodiment, the handle body 416 is positioned over the guide 468 and coupled to the guide 468 via a pin 498 that is passed through an elongated slot 499 in the guide 468. As can be seen in FIG. 17, the elongated slot 499 is angled such that when the guide 468 is coupled to the scope 401, the slot 499 extends toward the T-connector 484 of the scope 401. This mating of the pin 498 with slot 499 allows a user to move the lever ring 422 in the direction of arrow N (or in the direction opposite of arrow N) to a maximum limit at which the pin 498 abuts a distal (or proximal) end of the elongated slot 499 to make fine adjustments to the position of the shaft 410 in the scope working channel 406. Specifically, in this embodiment, teeth on the ledge 496 and teeth on the surface 495 below pin 494 may engage to maintain the N direction of the shaft advance or withdrawal. The lever ring 422 is depressed in the direction of arrow M to open the end effector 414 during or after the movement of the sheath 412 in the N direction. When the hand force is removed from the lever ring 422, the second spring 450 will return the end effector 414 to a closed position or to capture a burden. The pin 498 is then returned to a center position within the slot 499 before the handle assembly 405 can be rotated back to the retracted device shaft 410 position of FIG. 15.

Although the present disclosure describes the use of retrieval devices utilized to engage stones, stone fragments, and/or other foreign objects in the kidney, ureter and/or bladder, references to a particular type of procedure, such as a ureteroscopy; device, such as a retrieval device; end effector, such as a basket; organ, such as a kidney; and/or object, such as a stone or stone fragment, are provided for convenience and not intended to limit this disclosure. Furthermore, the handle assemblies discussed herein can be configured to advance or retract a laser fiber as well as to operate two or more medical devices simultaneously or independently. The handle assemblies can also be configured to advance or retract and injection needle having a medical luer hub connector at its proximal end. Accordingly, the concepts described herein may be utilized for any analogous device or system.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A retrieval device comprising:
   a handle comprising:
      a slider movable relative to a body of the handle in a proximal direction and a distal direction; and
      an actuator coupled to the slider;
   a sheath coupled to the slider;
   a drive wire received within the sheath and including an end effector at a distal end of the drive wire, wherein the sheath is movable relative to the drive wire and the end effector in the proximal direction and the distal direction; and
   a guide member movably coupled to the handle, wherein the actuator is configured to rotate about the guide member to thereby move the slider in the proximal direction and the distal direction.

2. The retrieval device of claim 1, wherein the guide member is configured to couple the handle to a scope device.

3. The retrieval device of claim 1, wherein the guide member includes a pin positioned within an arced slot of the handle, and wherein the pin is movable within the arced slot.

4. The retrieval device of claim 3, wherein the pin is on a curved portion of the guide member.

5. The retrieval device of claim 3, wherein the guide member further includes a ledge, and wherein the actuator is configured to contact the ledge.

6. The retrieval device of claim 5, wherein the actuator includes a lever and a pin configured to abut the ledge.

7. The retrieval device of claim 1, wherein the actuator includes a lever, and wherein the lever is coupled to the slider via an arm.

8. The retrieval device of claim 1, wherein the handle is further movable in a linear direction relative to the guide member.

9. The retrieval device of claim 1, wherein the handle includes a pin that is received within a slot of the guide member.

10. The retrieval device of claim 1, wherein the actuator includes a ring.

11. A retrieval device comprising:
    a handle comprising:
       a slider movable in a proximal direction and a distal direction; and
       a lever coupled to the slider;
    a sheath coupled to the slider;
    a drive wire including an end effector at a distal end of the drive wire, wherein the drive wire and the end effector are received within the sheath, and wherein the sheath is movable relative to the drive wire and the end effector; and
    a guide member configured to couple the handle to a scope device, wherein the lever is configured to rotate about the guide member to thereby move the slider in the proximal direction and the distal direction.

12. The retrieval device of claim 11, wherein the guide member includes a pin movable within an arced slot of the handle.

13. The retrieval device of claim 11, wherein the guide member includes a ledge, and wherein the handle includes a pin configured to abut the ledge.

14. The retrieval device of claim 11, wherein the handle is movable in a linear direction relative to the guide member.

15. The retrieval device of claim 11, wherein the lever is a first actuator of the handle, and the handle further includes a second actuator configured to move the sheath relative to the drive wire and the end effector independent of the slider.

16. The retrieval device of claim 11, wherein the guide member includes an elongated slot.

17. A retrieval device comprising:
a handle comprising:
  a slider movable in a proximal direction and a distal direction; and
  a lever coupled to the slider and configured to move the slider in the proximal direction and the distal direction;
a sheath coupled to the slider;
a drive wire received within the sheath and including an end effector at a distal end of the drive wire, wherein the sheath is movable relative to the drive wire and the end effector in the proximal direction and the distal direction via the slider; and
a guide member configured to couple the handle to a scope device, wherein the handle is configured to rotate about the guide member to thereby move the sheath, the drive wire, and the end effector relative to the guide member.

18. The retrieval device of claim 17, wherein the handle is further movable in a linear direction relative to the guide member.

19. The retrieval device of claim 17, wherein the guide member includes a pin on a curved portion of the guide member and movable within an arced slot of the handle, and wherein the handle includes a pin movable within a slot of the guide member.

20. The retrieval device of claim 17, wherein the guide member includes a ledge, and wherein the lever is configured rotate relative to the guide member to contact the ledge.

* * * * *